United States Patent
D'Armiento et al.

(10) Patent No.: US 6,656,461 B1
(45) Date of Patent: Dec. 2, 2003

(54) THERAPEUTIC TREATMENT OF CHRONIC OBSTRUCTIVE PULMONARY DISEASE

(75) Inventors: Jeanine D'Armiento, New York, NY (US); Kazushi Imai, New York, NY (US)

(73) Assignee: The Trustees of Columbia University in the City of New York, New York, NY (US)

( * ) Notice: Subject to any disclaimer, the term of this patent is extended or adjusted under 35 U.S.C. 154(b) by 0 days.

(21) Appl. No.: 09/514,885

(22) Filed: Feb. 29, 2000

(51) Int. Cl.⁷ .......................... A61K 38/19; C07K 14/52

(52) U.S. Cl. .................. 424/85.1; 514/12; 530/300; 530/350

(58) Field of Search ..................... 514/12; 530/300, 530/350; 536/23.5; 424/89.1

(56) References Cited

U.S. PATENT DOCUMENTS 5,824,551 A 10/1998 Damme et al.

OTHER PUBLICATIONS

Yasuda et al. An increase of soluble Fas, an inhibitor of apoptosis, associated with progression of COPD. Respiratory Medicine, (Aug. 1998) 92(8) 993–9.*

Haslett C. Granulocyte apoptosis and its role in the resolution and control of lung inflammation. Am J Respir Crit Care Med. Nov 1999; 160(5 Pt 2):S5–11.*

Vignola et al. Evaluationm of apoptosis of eosinophils, macrophages, and T lymphocytes in mucosal biopsy specimens of patients with asthma and chronic brochitis. Journal of Allergy and Clinical Immunology, (Apr. 1999) 103 (4) 563–73.*

Goya et al. Identificaiton of CCR8 as the specific receptor for the human beta–chemokine 1–309: cloning and molecular characterization of murine CCR8 as the receptor to TCA–3. J Immunol. Feb. 1998 15; 160(4):1975–81.*

Murdoch et al. Chemokine receptors and their role in inflammation and infectious diseases. Blood 2000 May 15; 95(10):3032–43.*

Melkonyan et al. SARPs: a family of secreted apoptosis–related proteins. Proc Natl Acad Sci U S A. Dec. 1997 9;94(25):13636–41.*

Imai et al. Activation of an embryonic gene product in pulmonary emphysema: identification of the secreted frizzled–related protein. Chest. May 2000; 117(5 Suppl 1):229S.*

Proost et al. Human monocyte chemotactic proteins–2 and –3: structural and functional comparison with MCP–1. J Leukoc Biol. Jan. 1996;59(1):67–74.*

Cardone MH, et al.: Regulation of Cell Death Protease Caspase–9 by Phosphorylation. *Science*. vol. 282, No. 5392, Nov. 13, 1998, pp. 1318–1321 (Exhibit 2).

D'Armiento J, et al.: Collagenase Expression in the Lungs of Transgenic Mice Causes Pulmonary Emphysema. *Cell*. vol. 71, No. 6, Dec. 11, 1992, pp. 955–961 (Exhibit 3).

Dale TC: Signal transduction by the Wnt family of ligands. *Biochem. J.* (1998), vol. 329, pp. 209–223 (Exhibit 4).

Dunnill MS, et al.: Quantitative Methods In The Study Of Pulmonary Pathology. *Thorax*. vol. 17, 1962, pp. 320–328 (Exhibit 5).

Feinleib M, et al.: Trends in COPD Morbidity and Mortality in the United States. *Am. Rev. Respir. Dis.* vol. 140, No. 3, Pt. 2, Sep. 1989, pp. S9–S18 (Exhibit 6).

Finch, PW, et al.: Purification and molecular cloning of a secreted, Frizzled–related antagonist of Wnt action. *Proc. Natl. Acad. Sci. USA*. vol. 94, Jun. 24, 1997, pp. 6770–6775 (Exhibit 7).

Frisch SM and Ruoslahti E: Integrins and Anoikis. *Curr. Opin. in Cell Biol.* vol. 9, No. 5, Oct. 1997, pp. 701–706 (Exhibit 8).

From the centers for disease control and prevention: Mortality Patterns–United States, 1991. *JAMA*. vol. 270, No. 24, Dec. 22, 1993, pp. 2916–2917 (Exhibit 9).

Granville DJ, et al.: Apoptosis: Molecular Aspects of Cell Death and Disease. *Lab. Invest.* vol. 78, No. 8, Aug. 1998, pp. 893–913 (Exhibit 10).

Hautamaki RD, et al.: Requirement of macrophage elastase for cigarette smoke–induced emphysema in mice. *Science*. vol. 277, Sep. 26, 1997, pp. 2002–2004 (Exhibit 11).

Hoang B, et al.: Primary structure and tissue distribution of FRZB, a novel protein related to Drosophilia frizzled, suggest a role in skeletal morphogenesis. *J Biol Chem*. vol. 271, No. 42, Oct. 18, 1996, pp. 26131–26137 (Exhibit 12).

Hoidal JR and Niewoehner DE: Pathogenesis of Emphysema. *Chest*. vol. 83, No. 4, Apr. 1983, pp. 679–685 (Exhibit 13).

(List continued on next page.)

*Primary Examiner*—David S. Romeo
(74) *Attorney, Agent, or Firm*—John P. White; Cooper & Dunham LLP

(57) ABSTRACT

The present invention provides a method of treating or preventing a chronic obstructive pulmonary disease in a subject, comprising administering to said subject an amount of an agent effective to inhibit apoptosis of the subject's lung cells and thus treat or prevent chronic obstructive pulmonary disease in the subject. The present invention provides for a method of identifying a compound effective to treat or prevent a chronic obstructive pulmonary disease, comprising (a) contacting lung cells from a subject having a chronic obstructive pulmonary disease with the compound and measuring the level of apoptosis of the lung cells in the presence of said compound, (b) measuring the level of apoptosis of the lung cells from the same subject in the absence of said compound, (c) comparing the level of apoptosis in step (a) with the level of apoptosis in step (b), wherein a higher level of apoptosis in step (a) indicate that the compound is effective to treat or prevent chronic obstructive pulmonary disease.

3 Claims, 19 Drawing Sheets

OTHER PUBLICATIONS

Imai K and D'Armiento J: Activation of an Embryonic Gene Product in Pulmonary Emphysema. *Am. Rev. Resp. Crit. Care Med.* vol. 159, 1983, p. A817 (Exhibit 14).

Imai K, et al.: Expression of Membrane–Type 1 Matrix Metalloproteinase and Activation of Progelatinase A in Human Osetoarthritic Cartilage. *Am. J. Pathol.* vol. 151, No. 1, Jul. 1997, pp. 245–256 (Exhibit 15).

Leyns L, et al.: Frzb–1 is a secreted antagonist of Wnt signaling expressed in the Spemann organizer. *Cell* vol. 88, No. 6, Mar. 21, 1997, pp. 747–756 (Exhibit 16).

Luisetti M, et al.: MR889, a neutrophil elastase inhibitor, in patients with chronic obstructive pulmonary disease: a double–blind, randomized, placebo–controlled clinical trial *Eur. Resp. J.* vol. 9, No. 7, Jul. 1996, pp. 1482–1486 (Exhibit 17).

Melkonyan HS, et al.: SARPs: A family of secreted apoptosis–related proteins. *Proc. Natl. Acad. Sci. USA.* vol. 94, No. 25, Dec. 9, 1997, pp. 13636–13641 (Exhibit 18).

Petitclerc E, et al.: Integrin $\alpha_\nu \beta_3$ Promotes M21 Melanoma Growth in Human Skin by Regulating Tumor Cell Survival. *Cancer Research.* vol. 59, No. 11, Jun. 1, 1999, pp. 2724–2730 (Exhibit 19).

Putt F: *Manual of Histopathological Staining Methods,* Wiley and Sons (New York), (1972), pp. 111–126 (Exhibit 20).

Rattner A, et al.: A family of secreted proteins contains homology to the cysteine–rich ligand–binding domain of frizzled receptors. *Proc Natl Acad Sci USA.* vol. 94, No. 7, Apr. 1, 1997, pp. 2859–2863 (Exhibit 21).

Rudin CM and Thompson CB: Apoptosis and Disease: Regulation and Clinical Relevance of Programmed Cell Death. *Annu. Rev. Med.* vol. 48, 1997, pp. 267–281 (Exhibit 22).

Shapiro SD: The Pathogenesis of Emphysema: the Elastase: Antielastase Hypothesis 30 years later. *Proc. Ass. Amer. Phys.* vol. 107, No. 3, Oct. 1995, pp. 346–352 (Exhibit 23).

Snider GL: Chronic Obstructive Pulmonary Disease: Risk Factors, Pathophysiology and Pathogenesis. *Annu. Rev. Med.* vol. 40, 1989, pp. 411–429 (Exhibit 24).

Snider GL, et al.: Pitfalls in Antiprotease Therapy of Emphysema. *Am. J. Respir. Crit. Care Med.* vol. 150, No. 6, Pt. 2, Dec. 1994, pp. S131–S137 (Exhibit 25).

Tetley TD: Proteinase imbalance: its role in the lung disease. *Thorax.* vol. 48, No. 5, May 1993, pp. 560–565 (Exhibit 26).

Tetsu O and McCormick F: b–catenin regulates expression of cyclin D1 in colon carcinoma cells. *Nature.* vol. 398, No. 6726, Apr. 1, 1999, pp. 422–426 (Exhibit 27).

Thurlbeck WM: Internal surface area and other measurements in emphysema. *Thorax.* vol. 22, No. 6, Nov. 1967, pp. 483–496 (Exhibit 28).

Tomkeieff SE: Linear Intercepts, Areas and Volumes. *Nature.* vol. 155, Jan. 6, 1945, p. 107 (Exhibit 29).

Wolf BB and Green DR: Suicidal Tendencies: Apoptotic Cell Death by Caspase Family Proteinases. *J. Biol. Chem.* vol. 274, No. 29, Jul. 16, 1999, pp. 20049–20052 (Exhibit 30).

Wyllie AH: Cell Death: The Significance of Apoptosis. *Int. Rev. Cytol.* vol. 68, 1980, pp. 251–306 (Exhibit 31).

Zhou Z, et al.: Up–Regulation of Human Secreted Frizzled Homolog in Apoptosis and its Down–Regulation in Breast Tumors. *Int. J. Cancer.* vol. 78, No. 1, Sep. 25, 1998, pp. 95–99 (Exhibit 32).

Vignola, AM et al., Evaluation of apoptosis of eosinophils, macrophages, and T lymphocytes in mucosal biopsy specimens of patients with asthma and chronic bronchitis, *J. Allergy Clin. Immunol,* Apr. 1999, pp. 563–573 (Exhibit 33).

Yasuda, N. An increase of soluble Fas, an inhibitor of apoptosis, associated with progression of COPD, *Respiratory Medicine* (1998), vol. 92, pp. 993–999 (Exhibit 34).

\* cited by examiner

FIGURE IF
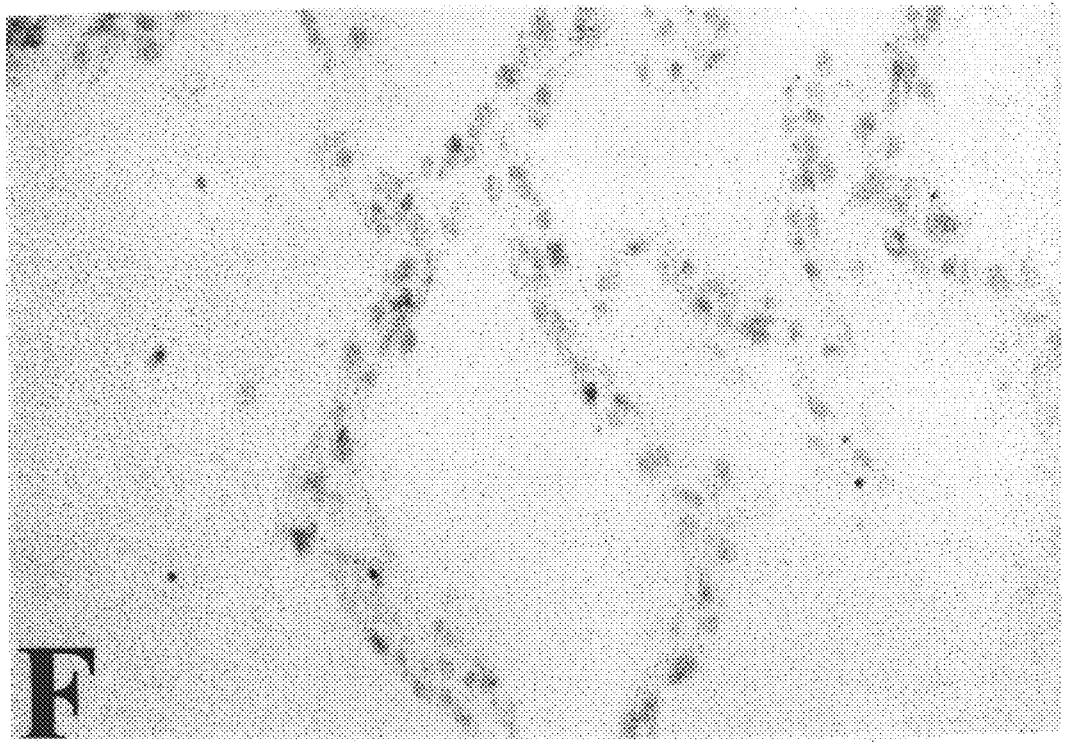

| Grade | Surface Area (mm²) | Apoptotic Index (%) |
|---|---|---|
| Normal-Mild | 179.8 ± 43.3 | 1.1 ± 1.4 |
| Moderate-Severe | 66.7 ± 18.9 | 7.5 ± 3.2 |

SEQUENCE LISTING

```
<160> NUMBER OF SEQ ID NOS: 2

<210> SEQ ID NO 1
<211> LENGTH: 313
<212> TYPE: PRT
<213> ORGANISM: Human

<400> SEQUENCE: 1

Met Gly Ile Gly Arg Ser Glu Gly Gly Arg Gly Ala Leu Gly Val
 1               5                  10                  15

Leu Leu Ala Leu Gly Ala Ala Leu Leu Ala Val Gly Ser Ala Ser Glu
                20                  25                  30

Tyr Asp Tyr Val Ser Phe Gln Ser Asp Ile Gly Pro Tyr Gln Ser Gly
            35                  40                  45

Arg Phe Tyr Thr Lys Pro Pro Gln Cys Val Asp Ile Pro Ala Asp Leu
    50                  55                  60

Arg Leu Cys His Asn Val Gly Tyr Lys Lys Met Val Leu Pro Asn Leu
65                  70                  75                  80

Leu Glu His Glu Thr Met Ala Glu Val Lys Gln Gln Ala Ser Ser Trp
                85                  90                  95

Val Pro Leu Leu Asn Lys Asn Cys His Ala Gly Thr Gln Val Phe Leu
                100                 105                 110

Cys Ser Leu Phe Ala Pro Val Cys Leu Asp Arg Pro Ile Tyr Pro Cys
            115                 120                 125

Arg Trp Leu Cys Glu Ala Val Arg Asp Ser Cys Glu Pro Val Met Gln
    130                 135                 140

Phe Phe Gly Phe Tyr Trp Pro Glu Met Leu Lys Cys Asp Lys Phe Pro
145                 150                 155                 160

Glu Gly Asp Val Cys Ile Ala Met Thr Pro Pro Asn Ala Thr Glu Ala
                165                 170                 175

Ser Lys Pro Gln Gly Thr Thr Val Cys Pro Pro Cys Asp Asn Glu Leu
                180                 185                 190

Lys Ser Glu Ala Ile Ile Glu His Leu Cys Ala Ser Glu Phe Ala Leu
            195                 200                 205

Arg Met Lys Ile Lys Glu Val Lys Lys Glu Asn Gly Asp Lys Lys Ile
    210                 215                 220
```

```
Val Pro Lys Lys Lys Pro Leu Lys Leu Gly Pro Ile Lys Lys
225             230                 235

Asp Leu Lys Lys Leu Val Leu Tyr Leu Lys Asn Gly Ala Asp Cys Pro
            245                 250                 255

Cys His Gln Leu Asp Asn Leu Ser His His Phe Leu Ile Met Gly Arg
            260                 265                 270

Lys Val Lys Ser Gln Tyr Leu Leu Thr Ala Ile His Lys Trp Asp Lys
            275                 280                 285

Lys Asn Lys Glu Phe Lys Asn Phe Met Lys Lys Met Lys Asn His Glu
            290                 295                 300

Cys Pro Thr Phe Gln Ser Val Phe Lys
305             310

<210> SEQ ID NO 2
<211> LENGTH: 2075
<212> TYPE: DNA
<213> ORGANISM: Human

<400> SEQUENCE: 2
cctgcagcct ccggagtcag tgccgcgcgc ccgccgcccc gcgccttcct gctcgccgca      60
cctccgggag ccggggcgca cccagcccgc agcgccgcct cccgccccgc gccgcctccg     120
accgcaggcc gagggccgcc actggccggg gggaccgggc agcagcttgc ggccgcggag     180
ccgggcaacg ctggggactg cgccttttgt ccccggaggt ccctggaagt ttgcggcagg     240
acgcgcgcgg ggaggcggcg gaggcagccc cgacgtcgcg gagaacaggg cgcagagccg     300
gcatgggcat cggcgcagc gaggggggcc gccgcgggc cctgggcgtg ctgctggcgc     360
tgggcgcggc gcttctggcc gtgggctcgg ccagcgagta cgactacgtg agcttccagt     420
cggacatcgg cccgtaccag agcgggcgct tctacaccaa gcacctcagt gcgtggaca     480 tccccgcgga cctgcggctg tgccacaacg tgggctacaa gatggtg ctgcccaacc     540 tgctggagca cgagaccatg gcggaggtga agcagcaggc cagcagctgg gtgcccctgc     600
tcaacaagaa ctgccacgcc gggacccagg tcttcctctg ctcgctcttc gcgcccgtct     660
gcctggaccg gccatctac ccgtgtcgct ggctctgcga ggccgtgcgc gactcgtgcg     720
agccggtcat gcagttcttc ggcttctact ggccccgagat gcttaagtgt gacaagttcc     780
cggaggggga cgtctgcatc gccatgacgc cgcccaatgc caccgaagcc tccaagcccc     840
aaggcacaac ggtgtgtcct ccctgtgaca acgagttgaa atctgaggcc atcattgaac     900
atctctgtgc cagcgagttt gcactgagga tgaaaataaa agaagtgaaa aagaaaatg      960 gcgacaagaa gattgtcccc aagaagaaga gcccctgaa gttggggccc atcaagaaga     1020
aggacctgaa gaagcttgtg ctgtacctga gaatggggc tgactgtccc tgccaccagc     1080
tggacaacct cagccaccac ttcctcatca tgggccgcaa ggtgaagagc cagtacttgc     1140
tgacggccat ccacaagtgg gacaagaaaa acaaggagtt caaaaacttc atgaagaaaa     1200
tgaaaaacca tgagtgcccc acctttcagt ccgtgtttaa gtgattctcc cgggggcagg     1260 gtgggagg agcctcgggt ggggtgggag cgggggggac agtgcccggg aacccgtggt     1320
cacacacacg cactgccctg tcagtagtgg acattgtaat ccagtcggct tgttcttgca     1380
gcattcccgc tcccttttccc tccatagcca cgctccaaac cccagggtag ccatggccgg     1440
gtaaagcaag ggccatttag attaggaagg tttttaagat ccgcaatgtg gagcagcagc     1500
cactgcacag gaggaggtga caaaccattt ccaacagcaa cacagccact aaaacacaaa     1560
aagggggatt gggcggaaag tgagagccag cagcaaaaac tacattttgc aacttgttgg     1620
```

-continued

```
tgtggatcta ttggctgatc tatgcctttc aactagaaaa ttctaatgat tggcaagtca    1680
cgttgttttc aggtccagag tagtttcttt ctgtctgctt taaatggaaa cagactcata    1740
ccacacttac aattaaggtc aagcccagaa agtgataagt gcagggagga aaagtgcaag    1800
tccattatct aatagtgaca gcaaagggac caggggagag gcattgcctt ctctgcccac    1860
agtctttccg tgtgattgtc tttgaatctg aatcagccag tctcagatgc cccaaagttt    1920
cggttcctat gagcccgggg catgatctga tccccaagac atgtggaggg gcagcctgtg    1980
cctgcctttg tgtcagaaaa aggaaaccac agtgagcctg agagagacgg cgattttcgg    2040
gctgagaagg cagtagtttt caaaacacat agtta                              2075
```

THERAPEUTIC TREATMENT OF CHRONIC OBSTRUCTIVE PULMONARY DISEASE

Throughout this application, various publications are cited by reference numbers. Full citations for these publications may be found listed at the end of the specification immediately preceding the claims. Certain references and publications are cited by full citation. The disclosures of these publications in their entireties are hereby incorporated by reference into this application in order to more fully describe the state of the art as known to those skilled therein as of the date of the invention described and claimed herein.

BACKGROUND OF THE INVENTION

Chronic obstructive pulmonary disease (COPD), consisting of emphysema and chronic bronchitis, is the fourth leading cause of death in the United States (1). Approximately 15 million Americans are affected by COPD and there is an increasing incidence in women(2). Smoking is the major risk factor for COPD and accounts for over 90% of cases seen worldwide. Despite the importance of the disease, there are no specific therapies available to limit or prevent the slow, progressive, destructive changes observed in COPD(3).

Currently the major hypothesis for the pathogenesis of emphysema is the protease-antiprotease theory(4,5). This model suggests that an imbalance between the levels of extracellular matrix degrading enzymes and their respective inhibitors damage the connective tissue matrix components of the lung. Studies over the past 30 years have demonstrated differences in the protease levels in the lung of patients with emphysema when compared to normal lung tissue(6). However, the molecular consequences of this finding have not been determined.

Although studies have demonstrated loss of the extracellular matrix in the lung of patients with emphysema, an investigation as to whether cell death contributes to the pathogenesis of this disease has not been performed.

SUMMARY OF THE INVENTION

The present invention provides a method of treating or preventing a chronic obstructive pulmonary disease in a subject, comprising administering to said subject an amount of an agent effective to inhibit apoptosis of the subject's lung cells and thus treat or prevent chronic obstructive pulmonary disease in the subject. The present invention provides for a method of identifying a compound effective to treat or prevent a chronic obstructive pulmonary disease, comprising (a) contacting lung cells from a subject having a chronic obstructive pulmonary disease with the compound and measuring the level of apoptosis of the lung cells in the presence of said compound, (b) measuring the level of apoptosis of the lung cells from the same subject in the absence of said compound, (c) comparing the level of apoptosis in step (a) with the level of apoptosis in step (b), wherein a higher level of apoptosis in step (a) indicate that the compound is effective to treat or prevent chronic obstructive pulmonary disease.

Panels A and B show hematoxylin and eosin staining of a normal lung (A) and the lung from an emphysema patient (B). The emphysema lung exhibits thinning of the alveolar wall, and a pronounced hypocellularity. The arrowhead identifies the nuclear pyknosis and fragmentation. In panel C–E, the TUNNEL reaction with fluorescein-incorporated dUTP was specifically observed in the emphysema lung specimen (D), but not in the normal counterpart (C). Panel E represents the reaction without TdT in the emphysema lung. The TUNNEL reaction with biotinylated dUTP localizes apoptotic cells to both the alveolar surface and mesenchyme of the emphysema lung (G). Note some macrophage-like cells contain TUNNEL-reactive material in their cytoplasm (inset). The normal lung was not stained (F). Bar: 50 $\mu$m (A, B, F and G), 100 $\mu$m (C–E) and 10 $\mu$m (inset in G).

Figure 2A:
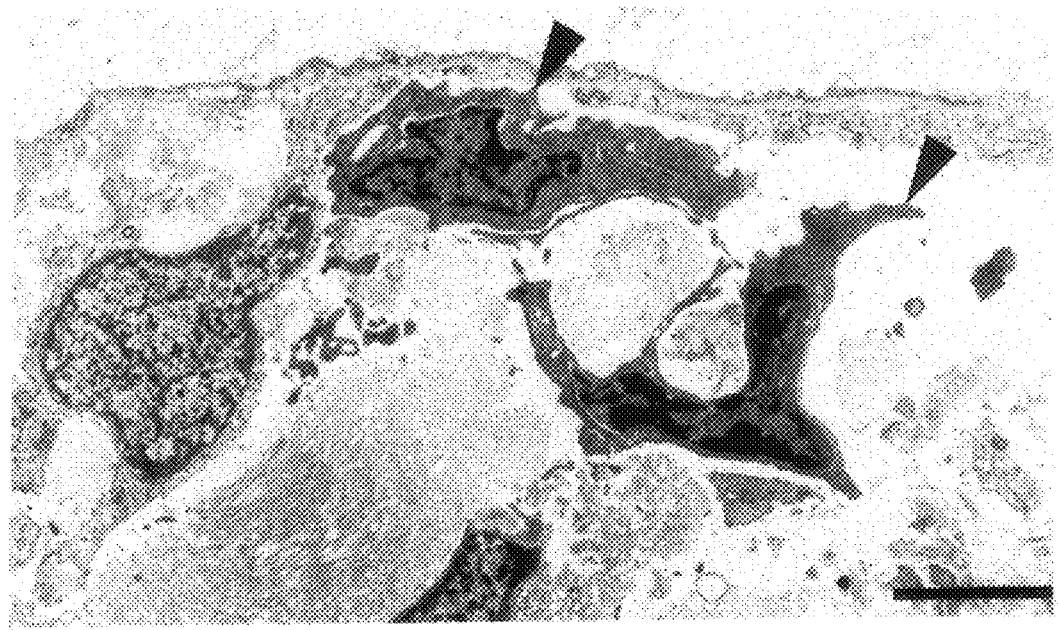

FIG. 2. Nuclear disruption in the emphysema lung samples.

A. Ultrastructure of the alveolar septum of the emphysema lung tissue. Apoptotic cells (arrowhead) adjacent to a normal cell (*) illustrate cytoplasmic condensation and shrinkage, with condensation of the nuclear chromatin. Loss of cell-extracellular matrix contact is also observed. Bar=2 $\mu$m. B. Isolated DNA from normal or emphysema lung tissues are electrophoresed on agarose gel (30 $\mu$g of DNA/lane) as described in the methods section. In contrast to high Mr intact DNA isolated from the normal lung samples (lanes 1–3), DNA from the emphysema lung samples shows a characteristic DNA laddering on the gel (lanes 4–7). Lane M indicates size of DNA by 1 kb ladder DNA marker.

FIG. 3. Morphometry and apoptotic index in lungs.

A. Surface area and apoptotic index in groups of normal or mild, and moderate to severe emphysema patients. A significant difference is seen between normal-mild and moderate-severe grades for surface area and apoptotic index ($p<0.01$). B. An inverse correlation between surface area and apoptotic index is observed by simple linear regression ($r2=0.605$).

FIG. 4. Caspase 3 and PARP cleavage in human lung tissue samples.

Tissue homogenates from normal (lanes 1–4) and emphysema lungs (lanes 5–8) were applied for the Western blot (120 g of total protein/lane) as described in METHODS. Lane 9 shows Jurkat cell lysates stimulated by anti-Fas antibody as a positive control. Expression of the pro-form of caspase 3 (32 kDa) is recognized by a monoclonal antibody to caspase 3 in panel A. The active species of 17 and 12 kDa with a 24 kDa intermediate form are specifically detected by a rabbit polyclonal antibody in the emphysema samples (panel B). The degradation product of PARP at 85 kDa is observed in the emphysema lung samples but not in the normal lung samples (panel C).

FIG. 5. Detection of Bax and Bad and silver staining in lung samples.

Normal (A, C and E) and emphysema lung specimens (B, D and F) are subjected to immunostaining for Bcl-2 (A and B), Bax (C and D) and Bad (E and F). In the emphysema samples Bax is immunolocalized to the alveolar surface epithelial cells (arrowheads) (D), while both mesenchymal (arrow) and alveolar surface epithelial cells (arrowhead) are recognized by the antibody to Bad (F). A high power view in panel D inset demonstrates inclusion of anti-Bax antibody-reacted material in a macrophage-like cell. Bar: 50 $\mu$m (A, B, E and F), 25 $\mu$m (C and D) and 10 $\mu$m (inset in D).

DETAILED DESCRIPTION OF THE INVENTION

The present invention provides a method of treating or preventing a chronic obstructive pulmonary disease in a subject, comprising administering to said subject an amount of an agent effective to inhibit apoptosis of the subject's lung cells and thus treat or prevent chronic obstructive pulmonary disease in the subject.

In one embodiment, the agent inhibits apoptosis by inhibiting an apoptotic pathway. In another embodiment of the invention, the agent inhibits the apoptotic pathway by inhibiting expression of the sFRP gene.

In another embodiment of the invention, the sFRP gene comprises a nucleic acid molecule comprising nucleotides having the sequence set forth in SEQ ID NO:1.

In another embodiment of the invention, the chronic obstructive pulmonary disease is emphysema.

In another embodiment of the invention, the chronic obstructive pulmonary disease is chronic bronchitis.

In another embodiment of the invention, the agent is selected from a group consisting of an antisense molecule, β chemokine, and a plant-derived composition.

In another embodiment of the invention, the antisense molecule comprises nucleic acid having 8–30 nucleotides.

In another embodiment of the invention, the β chemokine is β chemokine I-309.

In another embodiment of the invention, the β chemokine is β chemokine TCA-3.

In another embodiment of the invention, the agent is the Herpes simplex virus ICP4.

The present invention provides for a method of identifying a compound effective to treat or prevent a chronic obstructive pulmonary disease, comprising (a) contacting lung cells from a subject having a chronic obstructive pulmonary disease with the compound and measuring the level of apoptosis of the lung cells in the presence of said compound, (b) measuring the level of apoptosis of the lung cells from the same subject in the absence of said compound, (c) comparing the level of apoptosis in step (a) with the level of apoptosis in step (b), wherein a higher level of apoptosis in step (a) indicate that the compound is effective to treat or prevent chronic obstructive pulmonary disease.

In another embodiment of the invention, the level of apoptosis is determined by measuring DNA fragmentation or cleavage.

In another embodiment of the invention, the level of apoptosis is determined by measuring the expression of activated caspase 3.

In another embodiment of the invention, the level of apoptosis is determined by measuring the presence of poly (ADP ribose) polymerase.

In another embodiment of the invention, the level of apoptosis is determined by morphometric analysis.

In another embodiment of the invention, the level of apoptosis is determined by measuring Bcl-2 and Bad expression.

As used herein, the term "apoptosis" means programmed cell death or cell death caused by an active process of gene-directed cellular self-destruction and characterized by the rapid condensation of the cell with preservation of membranes, the compaction of chromatin, and DNA cleavage and fragmentation. The mechanism of apoptosis is described in detail in Granville D. J., et al. (1998) "Apoptosis: Molecular aspects of cell death and disease" Lab. Invest., 78:893–913 and the content of Granville D. J., et al. is fully incorporated in its entirety by reference.

As used herein, "Wnt gene" represents genes encoding Wnt glycoproteins which serve as inducers of cellular proliferation, migration, differentiation and tissue morphogenisis during normal development.

The term "FRP" means Frizzled-related Proteins which contain a region homologous to a putative Wnt-binding domain of Frizzleds and which serve as antagonists of Wnt action. The term "sFRP" means secreted Frizzled-related Proteins. One of the Frizzled-related Proteins or the secreted Frizzled-related Proteins is a polypeptide having an amino acid sequence set forth in SEQ ID NO:2 as follows:

```
MGIGRSEGGRRGALGVLLALGAALLAVGSASEYDYVSFQSDIGPYQSGRFYTKPPQCVD  (SEQ ID NO:1)

IPADLRLCHNVGYKKMVLPNLLEHETMAEVKQQASSWVPLLNKNCHAGTQVFLCSLFAP

VCLDRPIYPCRWLCEAVRDSCEPVMQFFGFYWPEMLKCDKFPEGDVCIAMTPPNATEAS

KPQGTTVCPPCDNELKSEAIIEHLCASEFALRMKIKEVKKENGDKKIVPKKKKPLKLGP

IKKKDLKKLVLYLKNGADCPCHQLDNLSHHFLIMGRKVKSQYLLTAIHKWDKKNKEFKN

FMKKMKNHECPTFQSVFK
```

The term "sFRP genes" means DNA molecules encoding Frizzled-related Proteins. One of the sFRP genes is a nucleic acid comprising nucleotides having the sequence as set forth in SEQ ID NO:2 as follows:

```
CCTGCAGCCT CCGGAGTCAG TGCCGCGCGC CCGCCGCCCC GCGCCTTCCT  (SEQ ID NO:2)

GCTCGCCGCA CCTCCGGGAG CCGGGGCGCA CCCAGCCCGC AGCGCCGCCT

CCCCGCCCGC GCCGCCTCCG ACCGCAGGCC GAGGGCCGCC ACTGGCCGGG

GGGACCGGGC AGCAGCTTGC GGCCGCGGAG CCGGGCAACG CTGGGGACTG

CGCCTTTTGT CCCCGGAGGT CCCTGGAAGT TTGCGGCAGG ACGCGCGCGG

GGAGGCGGCG GAGGCAGCCC CGACGTCGCG GAGAACAGGG CGCAGAGCCG

GCATGGGCAT CGGGCGCAGC GAGGGGGGCC GCCGCGGGGC CCTGGGCGTG
```

-continued

```
CTGCTGGCGC TGGGCGCGGC GCTTCTGGCC GTGGGCTCGG CCAGCGAGTA

CGACTACGTG AGCTTCCAGT CGGACATCGG CCCGTACCAG AGCGGGCGCT

TCTACACCAA GCCACCTCAG TGCGTGGACA TCCCCGCGGA CCTGCGGCTG

TGCCACAACG TGGGCTACAA GAAGATGGTG CTGCCCAACC TGCTGGAGCA

CGAGACCATG GCGGAGGTGA AGCAGCAGGC CAGCAGCTGG GTGCCCCTGC

TCAACAAGAA CTGCCACGCC GGGACCCAGG TCTTCCTCTG CTCGCTCTTC

GCGCCCGTCT GCCTGGACCG GCCCATCTAC CCGTGTCGCT GGCTCTGCGA

GGCCGTGCGC GACTCGTGCG AGCCGGTCAT GCAGTTCTTC GGCTTCTACT

GGCCCGAGAT GCTTAAGTGT GACAAGTTCC CGGAGGGGGA CGTCTGCATC

GCCATGACGC CGCCCAATGC CACCGAAGCC TCCAAGCCCC AAGGCACAAC

GGTGTGTCCT CCCTGTGACA ACGAGTTGAA ATCTGAGGCC ATCATTGAAC

ATCTCTGTGC CAGCGAGTTT GCACTGAGGA TGAAAATAAA AGAAGTGAAA

AAAGAAAATG GCGACAAGAA GATTGTCCCC AAGAAGAAGA AGCCCCTGAA

GTTGGGGCCC ATCAAGAAGA AGGACCTGAA GAAGCTTGTG CTGTACCTGA

AGAATGGGGC TGACTGTCCC TGCCACCAGC TGGACAACCT CAGCCACCAC

TTCCTCATCA TGGGCCGCAA GGTGAAGAGC CAGTACTTGC TGACGGCCAT

CCACAAGTGG GACAAGAAAA ACAAGGAGTT CAAAAACTTC ATGAAGAAAA

TGAAAAACCA TGAGTGCCCC ACCTTTCAGT CCGTGTTTAA GTGATTCTCC

CGGGGGCAGG GTGGGGAGGG AGCCTCGGGT GGGGTGGGAG CGGGGGGGAC

AGTGCCCGGG AACCCGTGGT CACACACACG CACTGCCCTG TCAGTAGTGG

ACATTGTAAT CCAGTCGGCT TGTTCTTGCA GCATTCCCGC TCCCTTTCCC

TCCATAGCCA CGCTCCAAAC CCCAGGGTAG CCATGGCCGG GTAAAGCAAG

GGCCATTTAG ATTAGGAAGG TTTTTAAGAT CCGCAATGTG GAGCAGCAGC

CACTGCACAG GAGGAGGTGA CAAACCATTT CCAACAGCAA CACAGCCACT

AAAACACAAA AAGGGGGATT GGGCGGAAAG TGAGAGCCAG CAGCAAAAAC

TACATTTTGC AACTTGTTGG TGTGGATCTA TTGGCTGATC TATGCCTTTC

AACTAGAAAA TTCTAATGAT TGGCAAGTCA CGTTGTTTTC AGGTCCAGAG

TAGTTTCTTT CTGTCTGCTT TAAATGGAAA CAGACTCATA CCACACTTAC

AATTAAGGTC AAGCCCAGAA AGTGATAAGT GCAGGGAGGA AAAGTGCAAG

TCCATTATCT AATAGTGACA GCAAAGGGAC CAGGGGAGAG GCATTGCCTT

CTCTGCCCAC AGTCTTTCCG TGTGATTGTC TTTGAATCTG AATCAGCCAG

TCTCAGATGC CCCAAAGTTT CGGTTCCTAT GAGCCCGGGG CATGATCTGA

TCCCCAAGAC ATGTGGAGGG GCAGCCTGTG CCTGCCTTTG TGTCAGAAAA

AGGAAACCAC AGTGAGCCTG AGAGAGACGG CGATTTTCGG GCTGAGAAGG

CAGTAGTTTT CAAAACACAT AGTTA
```

As used herein, the phrase "Chronic Obstructive Pulmonary Disease" means a process characterized by the presence of chronic bronchitis or emphysema that may lead to the development of airways obstruction, both reversible airways obstruction and irreversible airways obstruction. "Chronic obstructive pulmonary disease" includes chronic bronchitis, emphysema, and asthma.

As used herein, "inhibitors of cell apoptosis" includes, but not limited to, antisense compounds, such as described in Bennett, et al., U.S. Pat. No. 5,958,772, plant-derived compositions as described in Bathurst, et al., U.S. Pat. Nos. 5,620,885, 5,567,425, 5,624,672, 5,759,548 and 5,635,187, β chemokines, such as β chemokine I-309 and β chemokine TCA-3, as describe in Damme, et al., U.S. Pat. No. 5,824,551. "Inhibitors of cell apoptosis" also includes, but not limited to, and Herpes simplex virus ICP4 as described in Leopardi, et al., U.S. Pat. No. 5,876,923.

EXPERIMENTAL DETAILS

EXAMPLE 1

Apoptosis in Human Emphysema Lungs,
Implications for Novel Therapeutic Strategies Lung Samples: Human lung tissue was obtained between 1995–1999 from a total of 19 patients at Columbia Presbyterian Medical Center (IRB #X042 1) as follows: 14 samples were obtained from patients with emphysema who underwent lung transplant and five samples from patients who underwent lung volume reduction procedures. Samples from six normal lungs were used as controls. The six normal lung samples were obtained from donor lungs harvested from transplant but not used due to recipient complications or from accidental death victims. All of the emphysema samples were taken from patients who reportedly had stopped smoking for at least three months prior to harvesting the tissues. Cellular death was evaluated morphologically, histochemically and biochemically. Western blot analysis was performed to identify the presence of active caspase 3 and poly(ADP-ribose) polymerase in the emphysema tissue. Expression of the anti-apoptotic Bcl-2 protein, and its pro-apoptotic counterparts Bax and Bad were also determined through immunohistochemistry.

Histological Examination: After surgical excision, lungs were immediately fixed in 10% neutral buffered formalin for about 16 hours at 4° C. and embedded in paraffin-wax. Every sample was examined histologically in a blinded fashion for the presence of emphysema, fibrosis and inflammation and samples with pathological evidence of inflammation indicative of ongoing infection or neoplastic changes were excluded from this study. Sections (3 $\mu$m) were stained by silver impregnation for collagen fibrils(7,8). Immunohistochemical staining was performed using mouse IgG specific to human Bad (clone B31420, 10 g/ml) or Bcl-2 (clone B31420, 10 g/ml) (Transduction Laboratories, Lexington, Ky.) and rabbit polyclonal antibody to human Bax (clone 13666E, dilution×1,000. PharMingen, San Diego, Calif.). After incubation with biotinylated horse IgG to mouse IgG or goat IgG to rabbit IgG (Vector Laboratories, Burlingame, Calif.) and an avidin-biotin-peroxidase complex (DAKO, Glostrup, Denmark), color was developed with 3,3'-diaminobenzidine tetrahydrochloride. For transmission electron microscopy, tissues were cut into small pieces and fixed in 2.5% glutaraldehyde followed by 2% osmium tetroxide at 4° C. and processed to ultrathin sections for the electron microscope (1200 EX II, 80 KV, Jeol, Sundbyberg, Sweden).

In Situ Labeling of DNA Cleavage: Formalin-fixed specimens were subjected to oligonucleosomal fragment labeling of DNA by terminal deoxynucleotidyl transferase (TdT)-mediated X-dUTP nick end labeling (TUNNEL), using DeadEnd Colorimetric Apoptosis Detection System (Promega, Madison, Wis.) for streptavidin horseradish peroxidase-diaminobenzidine detection and In Situ Cell Death Detection Kit (Boehringer Mannheim, Indianapolis, Ind.) for fluorometric detection of apoptotic cells. These reactions were undertaken according to the manufacture's instructions. The percentage of TUNNEL reactive cells to total cells (apoptotic index) was measured in three different areas in each specimen at 40-fold magnification using light microscopy. The significance of difference in the apoptotic index between normal-mild emphysema and moderate-severe emphysema was determined by a Mann-Whitney U test. As a positive control, lung specimens were treated with RNase-free DNase I (Boehringer Mannheim) followed by TdT reaction. As a negative control, TdT was omitted from the reactions.

Morphometric Analysis: Tissue sections were stained with hematoxylin and eosin and the mean linear intercept and internal surface area were calculated according to established methods (9–11) using a light microscope linked to a Macintosh computer and Adobe Photoshop imaging software. A rectangular grid of dots at approximately 1 mm intervals was applied to 10 different areas in each section. From a random starting position on the grid, sequential and spaced images were digitally recorded for analysis. A test system was randomly superimposed upon each image. Horizontal lines were used to count alveolar surface intersections. Endpoints were used to calculate alveolar volumes. Results were analyzed with one-way analysis of the variance and simple linear regression was used for analysis of the relationship between surface area and apoptotic index.

DNA Fragmentation: Four emphysema and three normal lung tissues samples (100 mg of tissue wet weight) were digested with 0.1 mg/ml of Proteinase K for ~16 h in 1.2 ml of digestion buffer (10 mM Tris-HCl, 0.1 M NaCl, 25 mM EDTA, 0.5% SDS, pH 8.0). After protein extraction with phenol-chloroform isoamylalcohol and dialysis against 10 mM Tris-HCl, 1 mM EDTA, pH 8.0, samples were incubated with 1 $\mu$/ml of RNase A for 1 h at 37° C. and dialyzed in 10 mM Tris-HCl, 1 mM EDTA, pH 8.0, at 4° C. For detection of DNA fragmentation, 30 $\mu$g of isolated DNA were size fractionated on 1.4% agarose gel containing 0.1 $\mu$g/ml of ethidium bromide.

Protein Preparation and Analysis: Tissue homogenates of six emphysema and five normal lungs were prepared in 20 mM Tris-HCl, pH 7.4, 0.15 M NaCl, 0.02% NaN3, 1% NP-40, 1 mM PMSF, 2 mM N-ethylmaleimide, 10 $\mu$g/ml of leupeptin, 1 $\mu$g/ml of aprotinin, 10 $\mu$g/ml of pepstatin A, 10 $\mu$M E-64 and 1 mM EDTA. Proteins (120 $\mu$g) in the homogenate was size fractionated on SDS-PAGE under reducing conditions and electrotransferred onto a nitrocellulose membrane (Trans-Blot, BioRad, Hercules, Calif.). For immunological detection of proteins, Western blot was performed using mouse IgG to human caspase 3, clone C31720, 0.4 $\mu$g/ml (Transduction Laboratories) or polyclonal rabbit anti-human caspase 3 (PharMingen, Clone 67341A, 1 $\mu$g/ml) as previously described (12). Rabbit antibody against the proteolytic fragment of poly(ADP-ribose) polymerase (PARP) (Promega, Clone G734, 0.35 $\mu$g/ml) was also used.

Fluorometric Assay: Four emphysema and four normal lung tissues were homogenized in 20 mM Tris-HCl, pH 7.4, 10 mM Na2P2O7, 100 mM NaF, 2 mM NaVO4, 5 mM EDTA, 1 mM PMSF, 10 $\mu$g/ml aprotinin, and 1% NP-40. After removal of insoluble materials, caspase 3 activity was quantified by the fluorometric assay using specific synthetic peptide substrate (Ac-DEVD-AMC, PharMingen) as previously described(13).

Figure 1A:
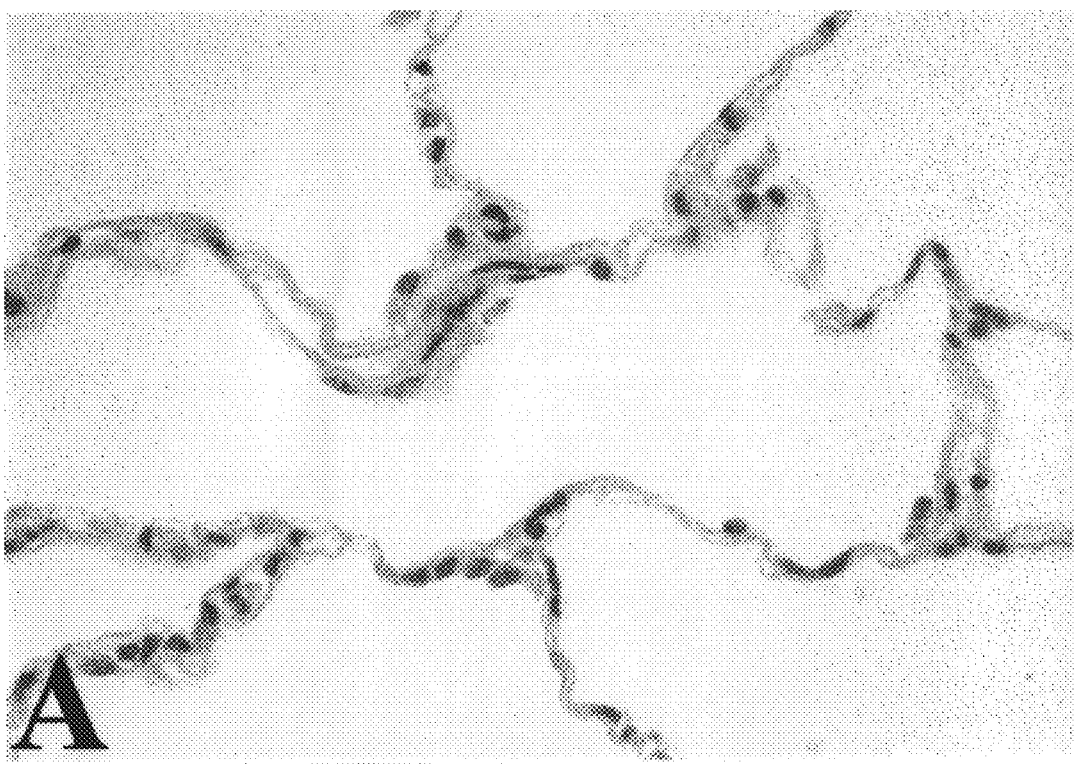
FIG. 1. Light micrographs and TUNNEL staining of normal and emphysema lungs.
Figure 1B:
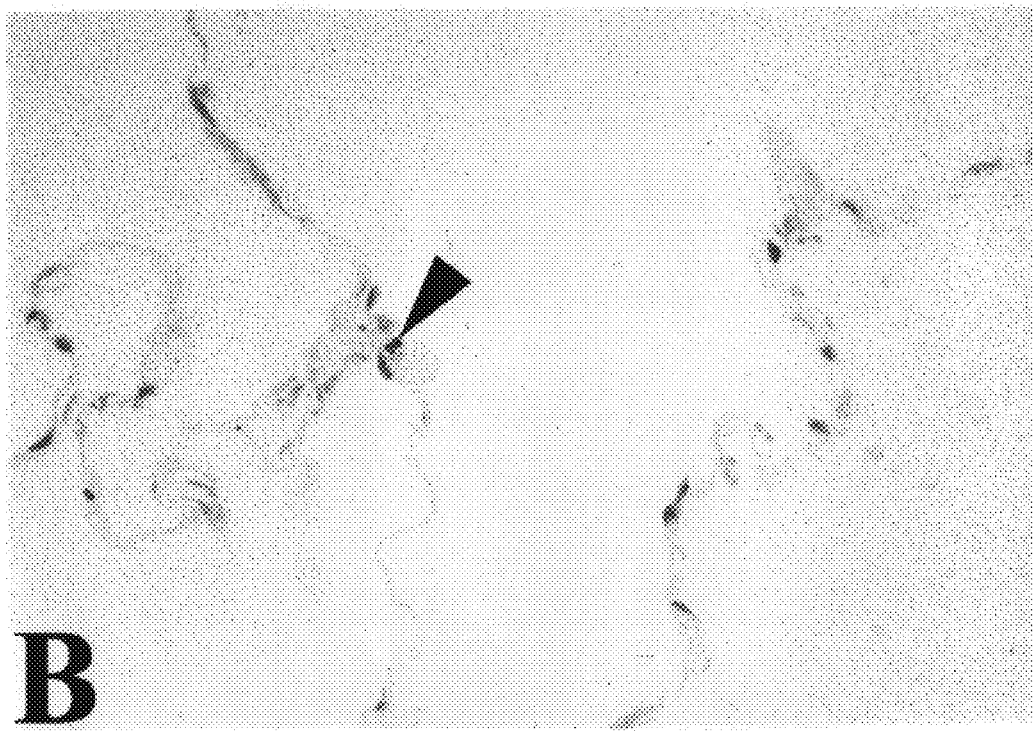

Morphological and Biochemical Detection of Apoptosis: In normal lungs, the alveolar wall consists of three tissue components including the surface epithelium, supporting connective tissue and blood vessels (FIG. 1A). The supporting tissue forms a layer beneath the epithelium and surrounding the blood vessels of the alveolar wall. In contrast, extensive loss of the alveolar architecture in the emphysema lungs is associated with hypocellularity and thinning of the remaining alveolar wall (FIG. 1B). Within the emphysema lung samples, cells were morphologically characteristic of cells undergoing apoptosis exhibiting convolution of nuclear outlines (FIG. 1B, arrow). These nuclear changes were observed in cells throughout the sample and not in focal regions as is seen in necrosis(14). The apoptotic cells included endothelial cells, epithelial cells and fibroblasts.

Neutrophil infiltration into the alveolar space or the alveolar septa was negligible.

Figure 1C:
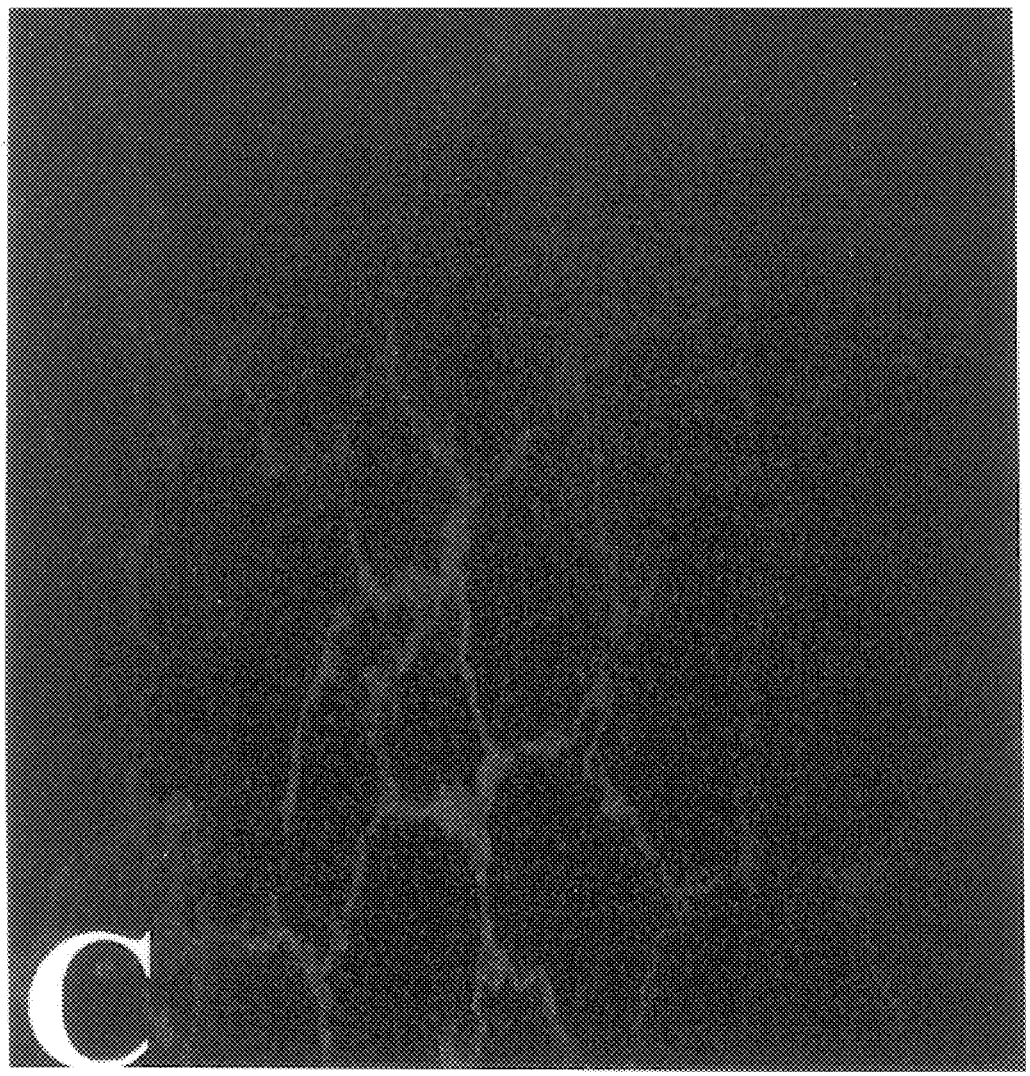
Figure 1D:
Figure 1E:
Figure 1G:
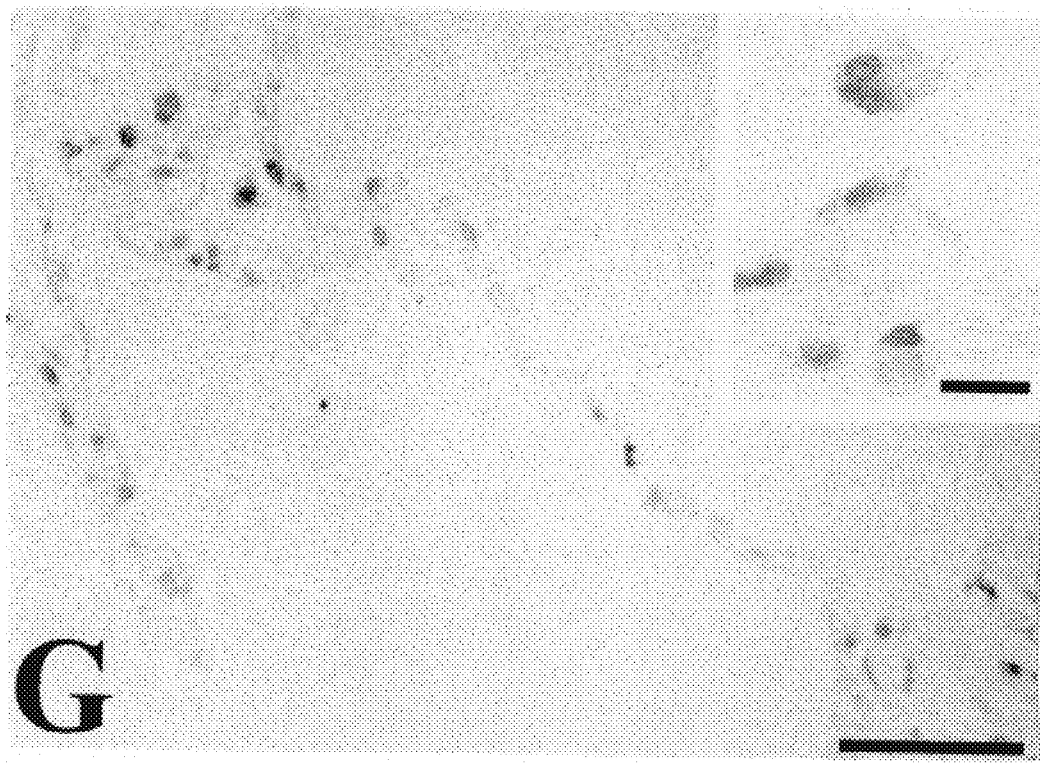

In Situ Detection of DNA Cleavage: To confirm the presence of apoptosis in the emphysema lung samples, two different TUNEL reactions were carried out. The first reaction using fluorescein-conjugated nucleotide exhibited little or no labeling in the normal lung tissue samples (FIG. 1C) while many cells with intense labeling were present throughout the emphysema tissue (FIG. 1D). Another TUNEL assay was performed using biotinylated nucleotide to identify the apoptotic cell type under the light microscope. Normal lung specimens did not react to TUNEL staining (FIG. 1F). In contrast to normal tissues, emphysema sections were TUNEL positive, however, there was no prevalent cell type. Throughout the emphysema lung specimen, alveolar and mesenchymal cells both exhibited positive TUNEL staining (FIG. 1G). In the emphysema tissue section, $6.1 \pm 3.5\%$ (mean$\pm 1$ S.D.) of cells were labeled (varied in cases from $1.3 \pm 0.3$ to $12.2 \pm 3.5$), whereas very few cells were positive in the normal lung samples ($0.1 \pm 0.1\%$) ($p<0.01$). Several macrophage-like cells were TUNEL-reactive in their cytoplasm characteristic of phagocytosis of apoptotic cell bodies (FIG. 1G, inset).

Ultrastructural analysis of the emphysema lung tissue demonstrated morphological changes consistent with apoptosis in several cell types. The most prominent feature seen was cytoplasmic condensation and vacuolization, chromatin condensation and connective tissue degradation. A representative example can be seen in FIG. 2A with two apoptotic cells (arrows) in close apposition to a healthy cell; note the cytoplasmic condensation and nuclear condensation in the apoptotic cell with irregularities in the cell shape.

Figure 2B:
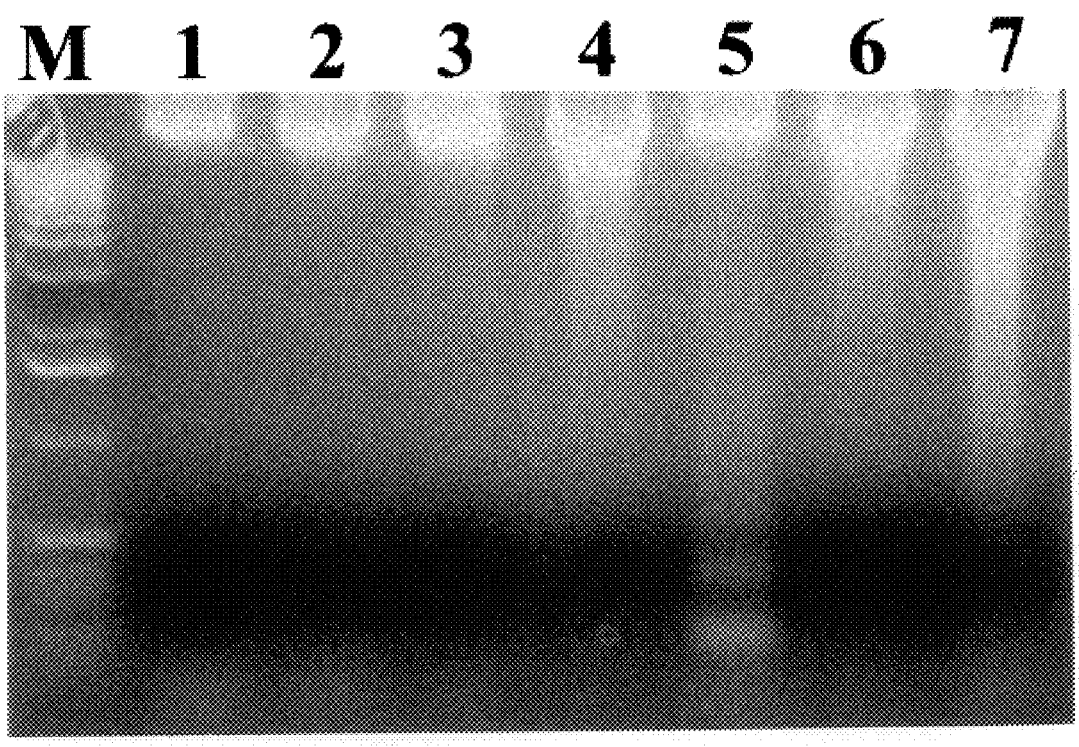

The presence of apoptosis in the emphysema lung samples was confirmed using biochemical analysis of DNA laddering (FIG. 2B). Electrophoresis of DNA isolated from emphysema tissues demonstrated degradation into small laddering fragments of multiples of approximately 180 bp subunit in contrast to the intact high Mr size seen in the normal samples.

Figures 3A, 3B:
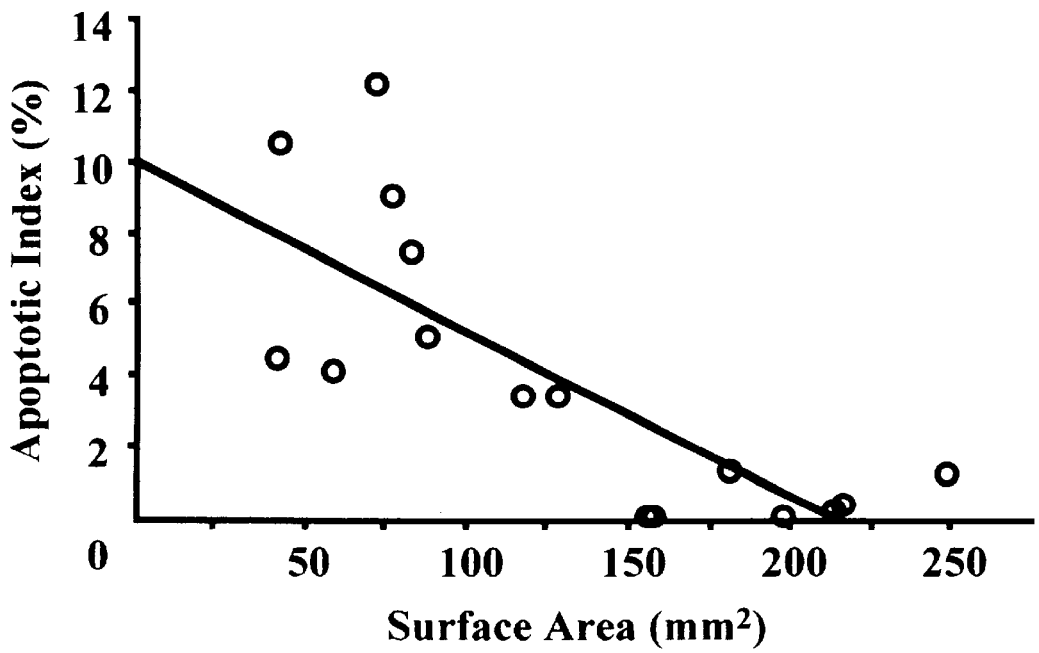

Correlation of morphometric measurements with apoptotic index Morphometric studies were performed on lung tissue examined in the above studies and surface area was calculated for each sample. Samples were divided into groups according to the severity of emphysema based on surface area measurements. There was a statistically significant association between the apoptotic index and emphysema severity ($p<0.01$) (FIG. 3A). In addition, through regression analysis the apoptotic index was shown to inversely correlate with the surface area demonstrating an increase in apoptosis with decreased surface area (FIG. 3B)

Figure 4A:
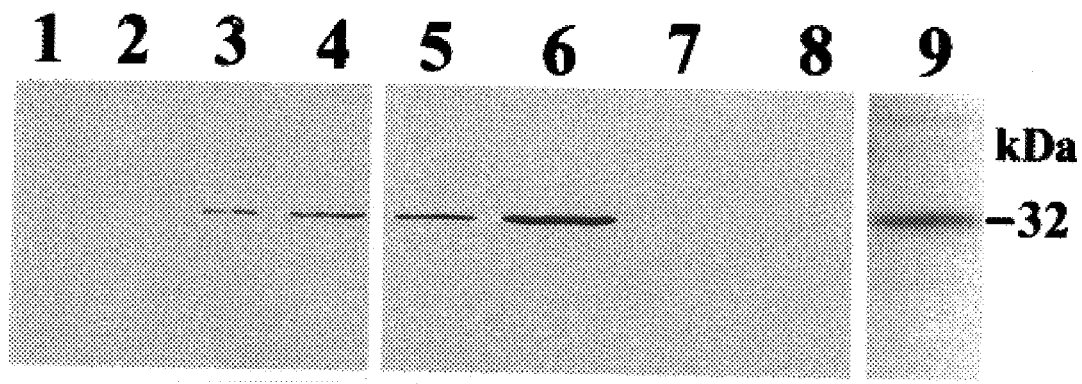
Figure 4B:
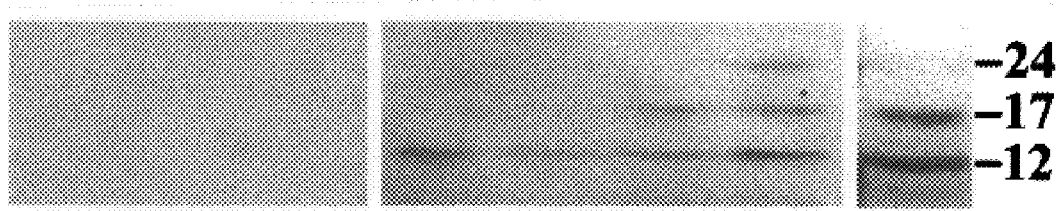
Figure 4C:
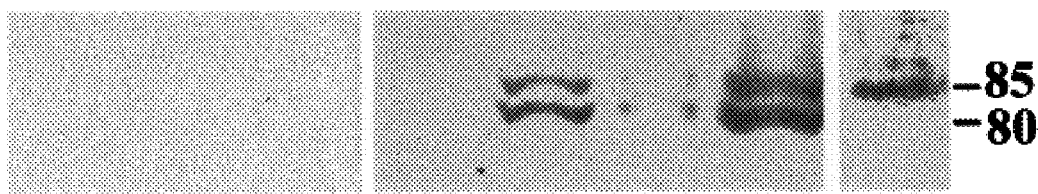

Caspase Expression and Activity in Lung Homogenates: Aspartate-directed cysteine proteases, caspases, play a pivotal role in execution of the apoptotic pathway, but not in necrosis(15). In order to detect caspase expression, we subjected tissue homogenates directly to Western blot analysis. As shown in FIG. 4A, pro-caspase 3 (32 kDa) was detected in both normal and emphysema lung homogenates with no clear difference in expression levels in these samples. This result was confirmed by reactivity with a rabbit polyclonal antibody against caspase 3 (data not shown). The activated subunits of caspase 3 (p17 and p12) were, however, only detected in the emphysema lung homogenates (FIG. 4B). In addition, an antibody that specifically reacts to the proteolytic fragment of PARP, a substrate of caspase 3, demonstrated reactivity in the emphysema lung tissue homogenates but not in normal lung tissues (FIG. 4C).

Using a fluorogenic synthetic peptide substrate caspase 3 activity was detected in the emphysema lung homogenates and not in normal lung homogenates (data not shown).

Figure 5A:
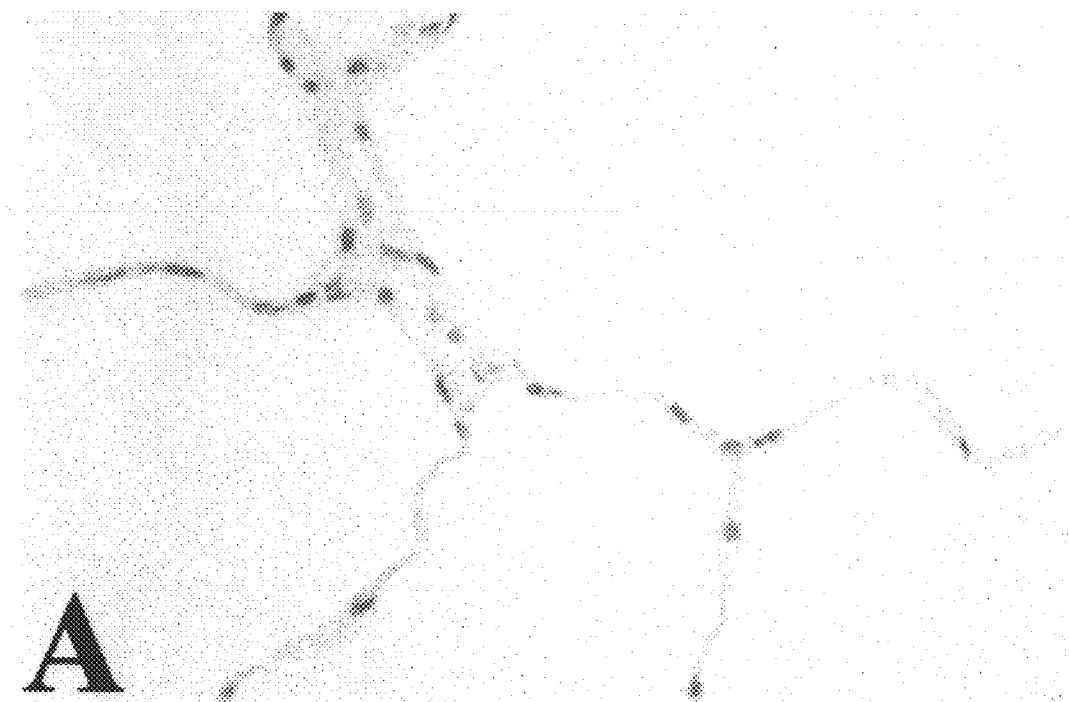
Figure 5B:
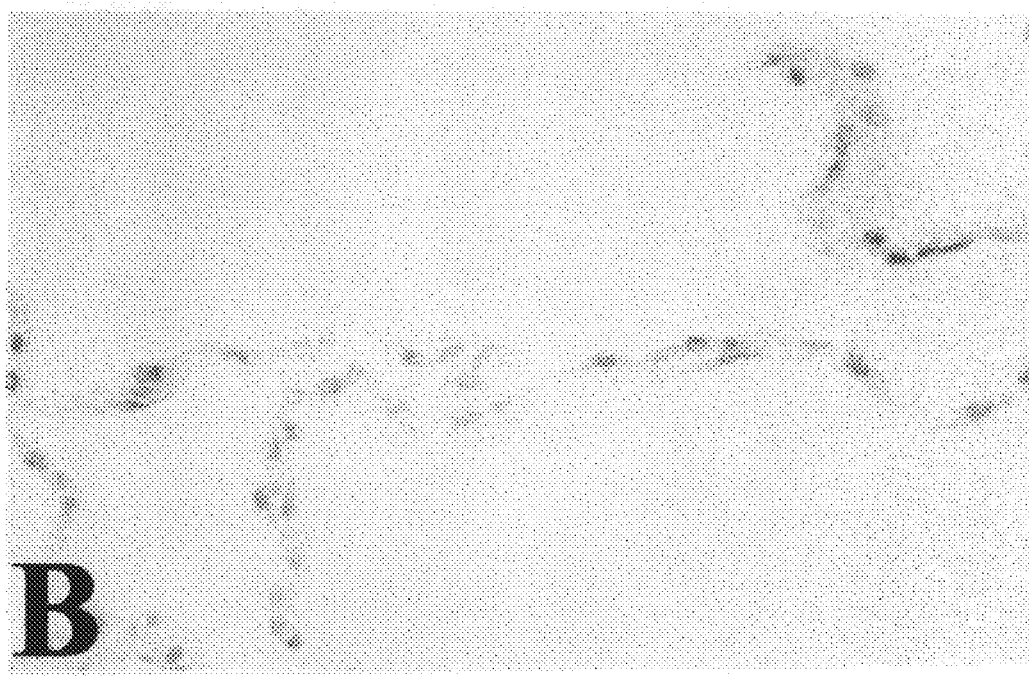
Figure 5C:
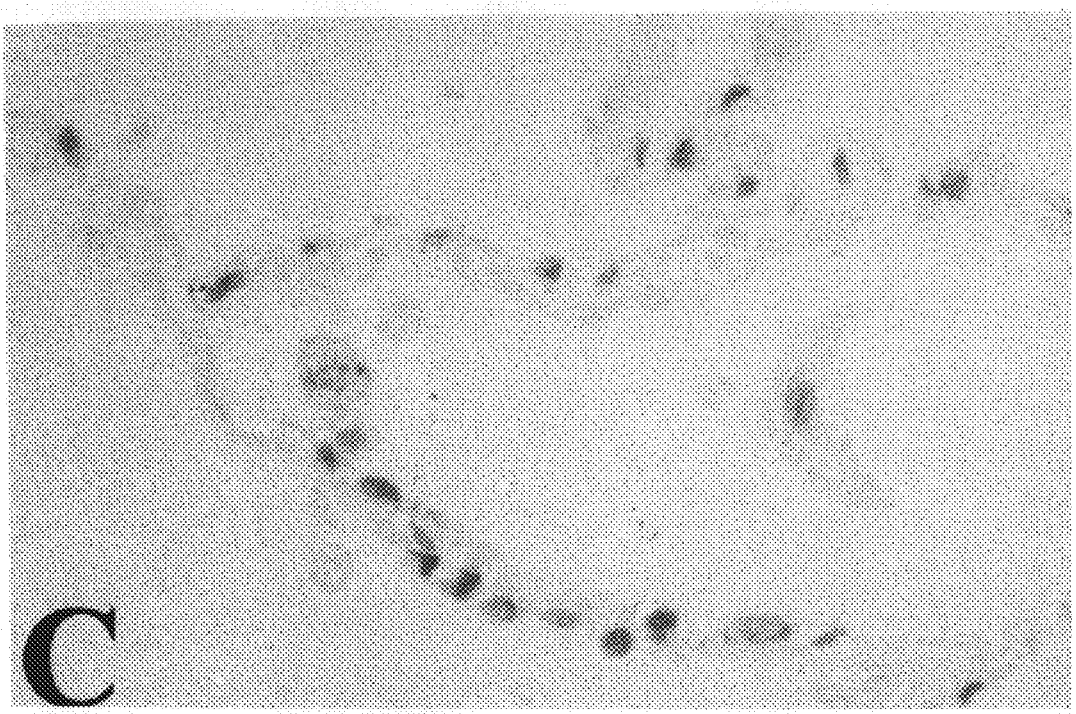
Figure 5D:
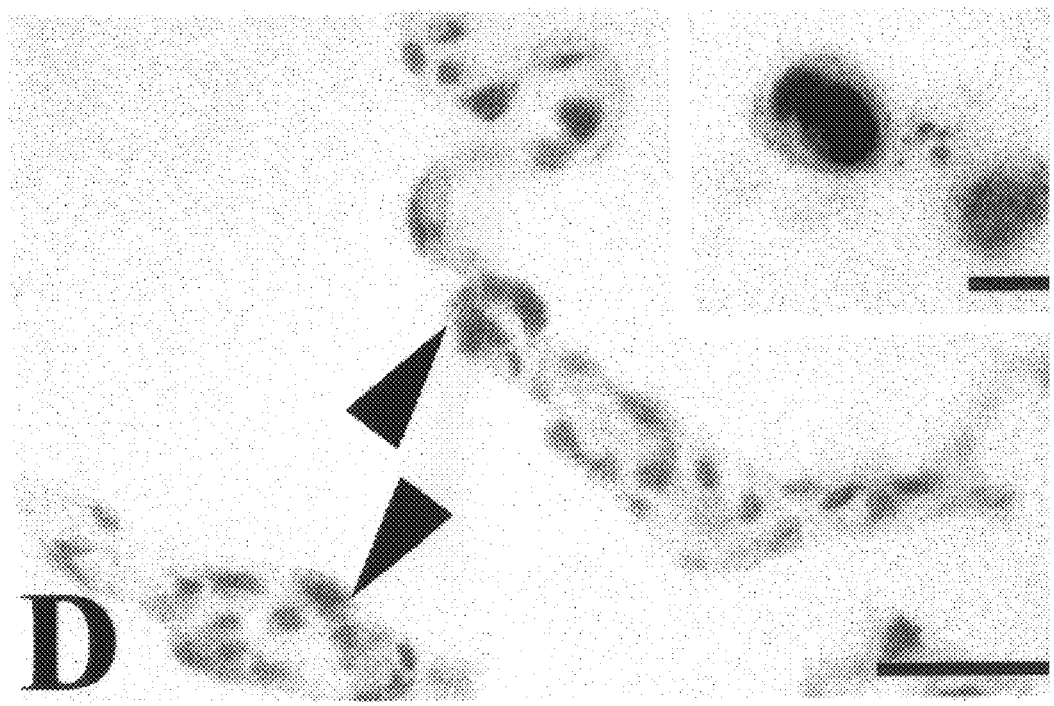
Figure 5E:
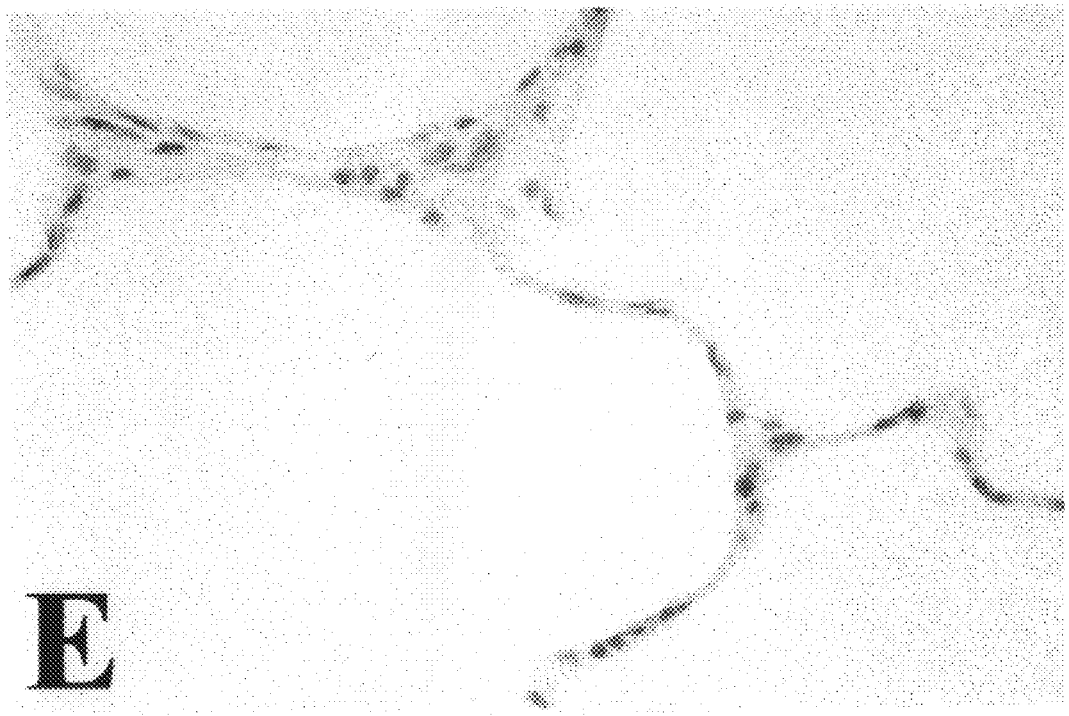
Figure 5F:
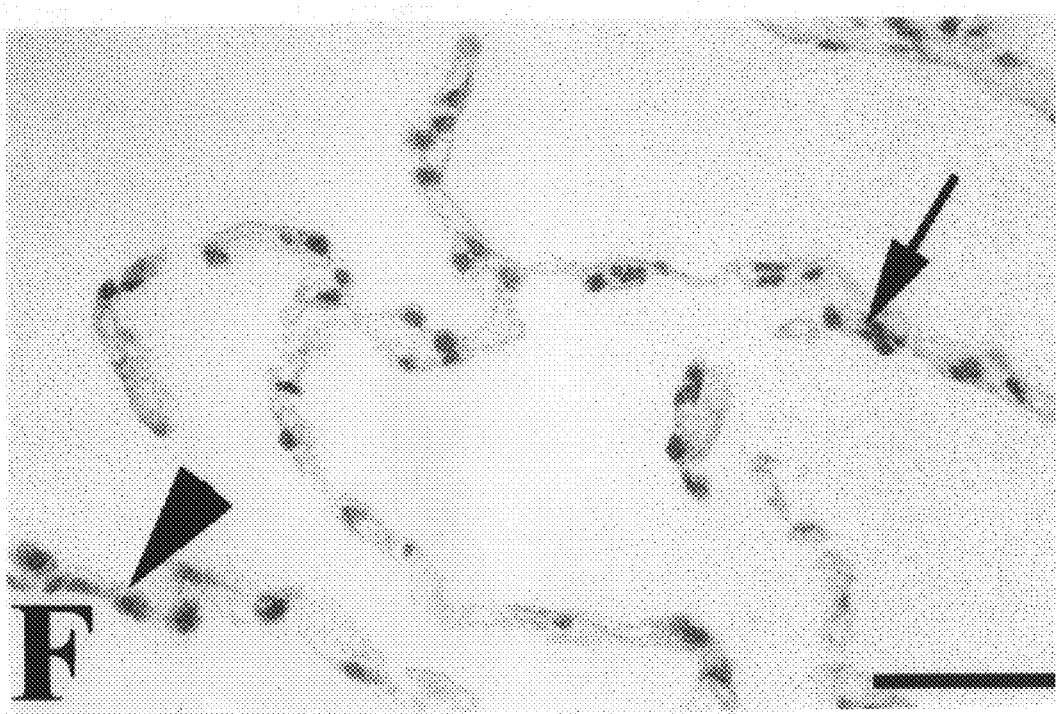

Bcl-2 and Bad Expression and Degradation of Collagen Fibrils: Recent studies indicate that the ratio of Bax protein expression to Bcl-2 expression is increased in apoptotic cells, especially when cells loose contact with extracellular matrix attachment(16, 17). Immunohistochemical analysis to detect the expression of Bcl-2, Bax and Bad was performed. Although Bcl-2 was not detected in either normal or emphysema lung tissue (FIGS. 5A and 5B), Bax and Bad reactivity was seen only in the emphysema lung samples (FIGS. 5C–F). Bax staining was localized to the epithelial cells in the emphysema lung samples (FIG. 5D, arrow, inset), whereas Bad staining was localized randomly to the epithelial and mesenchymal cells (FIG. 5F). This immunolocalization of Bad is consistent with the pattern of the TUNEL reaction. The normal lung tissue was negative for Bad immunostaining (FIG. 5E).

Discussion

In the present study, we examined morphological changes, DNA fragmentation, caspase activation and connective tissue degradation in human emphysema and normal lung tissues. Chronic obstructive pulmonary disease (COPD) is believed to be caused by exposure to cigarette smoke. However, the cellular mechanisms responsible for the progressive deterioration of respiratory function in COPD remain unclear and appear to result from architectural destruction including cellular disruption that may be associated with apoptosis. Our results demonstrate extensive cell death through apoptosis in the emphysema lungs.

Emphysema is postulated to develop from disruption of the extracellular matrix through an imbalance between proteases and antiproteases(6, 18). In the present study, we demonstrated for the first time that there is extensive cell death by apoptosis in combination with connective tissue degradation in the human emphysema lung. In this chronic disease there is progressive deterioration of lung function which could be accounted for by apoptosis.

Two different mechanisms, i.e., necrosis and apoptosis are observed in cellular death. The two processes can be distinguished by distinct morphological features. Necrotic cells exhibit several characteristic features such as cellular swelling and rupture of the plasma membrane, while the nucleus remains relatively intact. Necrosis is usually associated with an inflammatory reaction which develops in the adjacent viable tissue in response to the release of cellular debris. On the other hand, cell shrinkage and blebbing, chromatin condensation and nuclear fragmentation, and intact cytoplasmic organelles morphologically characterize apoptotic cells(14). The morphological features of the emphysema lung cells in this study are consistent with apoptosis. In addition, we found evidence of DNA fragmentation in lung samples from patients with emphysema on the basis of both in situ end labeling and gel electrophoresis. The histological analysis and the TUNEL assay demonstrated no specificity in cell-types undergoing apoptosis. However, these observations are based on tissue samples at the end stage of the disease. We frequently observed TUNEL-positive material-containing macrophages in the emphysema specimens, suggesting a role for alveolar macrophages as a scavenger of apoptotic cells.

Caspase-3 processing into active species in the emphysema lung tissue, but not in the normal lung, strongly supports our observation of ongoing apoptosis in the emphysema lungs. Exclusive caspase 3 activity against a synthetic peptide in the emphysema samples confirms this observation. The sequence of caspase activation is an indispensable process in the apoptosis pathway(19). Caspase 3 functions down-stream of cell damage in the apoptotic pathway and has a pivotal role in targeting molecules for proteolysis. Proteolysis of PARP by caspase 3 is a specific event that occurs during apoptosis(19). Detectable degradation of PARP into an 85 kDa fragment was observed in the emphysema tissue samples indicating caspase activity in the emphysema tissues but not in the normal lungs.

The close correlation of apoptosis with the morphological parameters of the disease was demonstrated in this study. Although the apoptotic index was variable between patient samples, statistical analysis demonstrates that the increase in apoptotic cell death associates with more severe structural destruction of the lung. When comparing the apoptotic index with morphometric measurements of emphysema this study strongly demonstrates a correlation between apoptosis and severity of disease and emphasizes the potential involvement of apoptosis in emphysema progression. The direct mechanism of apoptosis in human studies is not easily identifiable, however, intuitively the disruption of the extracellular matrix through the known protease-antiprotease imbalance could lead to induction of the cellular death program. The presence of apoptosis in the lung does not negate the role of proteases in the pathogenesis of the disease and may be a continuum in the process of destruction. The failure of the lung to maintain its cellular architecture in the presence of excess proteases may ultimately lead to the induction of apoptosis. It is known that expression of pro-apoptotic Bax family members is increased when cells are dying through depletion of cell adhesion to the extracellular matrix(16, 17) The Bax family members counteract Bcl-2 function and trigger caspase activation. Our immunostaining data suggests that there is an increase of Bax protein staining in contrast to Bcl-2 in the emphysema tissue. It is known that in emphysema tissue there is extensive loss of the extracellular matrix leading to massive connective tissue damage in the emphysema alveolus(20). Furthermore, TUNNEL positive staining was seen in a transgenic mouse model of emphysema (7) as compared to the wild-type litter mates (Imai et al, unpublished results). This transgenic model develops emphysema as a result of collagenase disruption of the extracellular matrix.(7) Immunoreactivity to anti-Bad antibody was also increased in the emphysema lungs. Although a role for increased Bad expression has not been defined, Bad is known to counteract Bcl-2 induced apoptosis. Therefore, the combination of increased Bax and Bad staining, increased apoptosis in the transgenic mouse and loss of the extracellular matrix in emphysema leads us to hypothesize that connective tissue degradation in the alveolar septa abrogates the cell-matrix attachment and contributes to induction of apoptosis.

Recently, we identified emphysema specific expression of secreted frizzled-related protein using a differential display assay(21). This molecule inhibits Wnt binding to its cell surface receptor frizzled. Although targeting of the Wnt signal in mammals is not well defined, expression of the exogenous Wnt gene in cultured cells promotes cellular proliferation(22). Interestingly, secreted frizzled-related protein was also identified as an apoptosis-inducing protein in cultivated cells(23, 24). Thus, the inhibition of the Wnt signaling pathway could possibly be involved in the apoptosis seen in the emphysema lung.

In the present study, we demonstrate for the first time that extensive apoptosis is occurring in emphysema lung. This is an intriguing novel mechanism in which to explain the destruction of the lung during progression of the disease. This is the first demonstration in emphysema that cellular loss in addition to matrix loss plays a role in the disease process. Recent studies demonstrated that apoptosis is occurring in a variety of chronic human diseases including neurodegenerative disease, heart failure, atherosclerosis, and viral diseases(19, 25). In several of these diseases, anti-apoptotic agents are expected to treat patients or slow disease progression and many of those agents are under evaluation and could potentially be applied to emphysema.

Conclusions

Lungs from all emphysema samples, but not normal controls, showed evidence of DNA fragmentation as determined by TUNNEL assays. In agreement with the positive TUNNEL assays, the emphysema lung samples also exhibited DNA indicative of cells undergoing apoptosis. Western blot analysis exhibited expression of activated caspase 3 and the presence of a specific cleavage product of poly(ADP-ribose) polymerase. Finally, immunohistochemistry demonstrated increased expression of pro-apoptotic molecules Bax and Bad in the emphysema lung samples with no increase in BCL-2.

The novel demonstration of apoptosis in the emphysema lung suggests that programmed cell death contributes to the progressive loss of respiratory function in this disease. Therefore, disrupting the apoptotic pathway could be an alternative approach to therapy in humans.

REFERENCES

1. From the centers for disease control and prevention. Mortality patterns-United States, 1991. JAMA, 1993, 270:2916–2917;
2. Feinleib M., et al. (1989) "Trends in COPD morbidity and mortality in the United States" Am Rev Respir Dis., 140:S9–18;
3. Snider G. L. (1989) "Chronic obstructive pulmonary disease: risk factors, pathophysiology and pathogenesis" Annu. Rev. Med., 40:411–429;
4. Snider G. L., et al. (1994) "Pitfalls in antiprotease therapy of emphysema" Am. J. Respir Crit. Care Med., 150:S131–S137;
5. Tetley T. D. (1993) "Proteinase imbalance: its role in the lung disease" Thorax, 48:560–565;
6. Shapiro S. D. (1995) "The pathogenesis of emphysema: the elastase:antielastase hypothesis 30 years later" Proc. Ass. Amer. Phys., 107:346–353;
7. D'Armiento J. et al. (1992) "Collagenase expression in the lungs of transgenic mice causes pulmonary emphysema" Cell, 71:955–961;
8. Putt F. (1972) Manual of Histopathological Staining Methods. New York: Wiley and Sons, 111–126;
9. Dunnill N. S. (1962) "Quantitative methods in the study of pulmonary pathology" Thorax, 17:320–328;
10. Thurlbeck W. M. (1967) "Internal surface area and other measurements in emphysema" Thorax, 22:486–496;
11. Tomkeiff S. E. (1945) "Linear intercepts, area and volumes" Nature, 155:105–111;
12. Imai K., et al. (1997) "Expression of membrane-type 1 matrix metalloproteinase and activation of progelatinase A in human oeteoarthritic cartilage" Am. J. Pathol., 151:245–256;
13. Cardone M. H., et al. (1998) "Regulation of cell death protease caspase-9 by phosphorylation" Science, 282:1318–1321;

14. Wyllie A. H. (1980) "Cell death: The significance of apoptosis" Int. Rev. Cytol., 68:251–306;
15. Wolf B. B. and Green D. R. (199) "Suicidal tendencies: Apoptotic cell death by caspase family proteinases" J. Biol. Chem., 274:20049–20052;
16. Frisch S. M. and Ruoslahti E. (1997) "Integrins and anoikis" Curr. Opin. Cell Biol., 9:701–706;
17. Petitclerc E., et al. (1998) "Integrin V 3 promotes M21 melanoma growth in human skin by regulation tumor cell survival" Cancer Res., 59:2724–2730;
18. Luisetti M., et al. (1996) "MR889, a neutrophil elastase inhibitor, in patients with chronic obstructive pulmonary disease: a double-blind, randomized, placebo-controlled clinical trial" Eur. Resp. J., 9:1482–1486;
19. Granville D. J., et al. (1998) "Apoptosis: Molecular aspects of cell death and disease" Lab. Invest., 78:893–913;
20. Hoidal J. R. and Niewoehner D. E. (1983) "Pathogenesis of emphysema" Chest., 83:679–684;
21. Imai K. and D'Armiento J. (1999) "Activation of an embryonically expressed gene in pulmonary emphysema. Identification of the secreted frizzled-related protein" Am. Rev. Resp. Crit. Care Med., 159:A817;
22. Tetsu O. and McCormick F. (1999) β-catenin regulates expression of cyclin D1 in colon carcinoma cells. Nature 398:422–426;
23. Melkonyan H. S., et al. (1997) "SARPs: A family of secreted apoptosis-related proteins" Proc. Natl. Acad. Sci. USA 94:13636–13641;
24. Zhou Z., et al. (1998) "Up-regulation of human secreted frizzled homolog in apoptosis and its down-regulation in breast tumors" Int. J. Cancer, 78:95–99;
25. Ruddin C. M. and Thompson C. B. (1997) "Apoptosis and disease: Regulation and clinical relevance of programmed cell death" Annu. Rev. Med., 48:267–281;
26. Finch, P. W. et al. (1997) "Secreted frizzle related protein gene" Proc. Natl. Acad. Sci., 94:6770–6777.

What is claimed is:

1. A method of inhibiting apoptosis of lung cells in a patient afflicted with a chronic obstructive pulmonary disease comprising administering to the patient an anti-apoptotic β-chemokine.

2. The method of claim 1, wherein the chronic obstructive pulmonary disease is emphysema.

3. The method of claim 1, wherein the chronic obstructive pulmonary disease is chronic bronchitis.

* * * * *